(12) United States Patent
Brem

(10) Patent No.: US 8,030,537 B1
(45) Date of Patent: Oct. 4, 2011

(54) SOMATIC CLONING GENE TRANSFER FOR THE PRODUCTION OF RECOMBINANT PROTEINS, CELLS AND ORGANS

(75) Inventor: Gottfried Brem, Hilgertshausen (DE)

(73) Assignee: Apogene GmbH & Co. KG, Hilgertshausen (DE)

( * ) Notice: Subject to any disclaimer, the term of this patent is extended or adjusted under 35 U.S.C. 154(b) by 435 days.

(21) Appl. No.: 10/333,670

(22) PCT Filed: Jul. 27, 2000

(86) PCT No.: PCT/EP00/07239
§ 371 (c)(1),
(2), (4) Date: Jun. 19, 2003

(87) PCT Pub. No.: WO02/09507
PCT Pub. Date: Feb. 7, 2002

(51) Int. Cl.
*C12P 21/00* (2006.01)
*C12N 15/00* (2006.01)

(52) U.S. Cl. .................... 800/4; 800/24; 800/15

(58) Field of Classification Search .............. 800/4, 24
See application file for complete search history.

(56) References Cited

U.S. PATENT DOCUMENTS

| 5,639,457 A | 6/1997 | Brem et al. |
| 5,811,635 A | 9/1998 | Goldstein et al. |

FOREIGN PATENT DOCUMENTS

| WO | WO 94/24853 | 11/1994 |
| WO | WO 94/27622 | 12/1994 |
| WO | WO 96/39811 | 12/1996 |
| WO | WO 98/30683 | 7/1998 |
| WO | WO 98/37183 | 8/1998 |
| WO | WO 98/58963 | 12/1998 |
| WO | WO 99/09141 | 2/1999 |
| WO | WO 99/35906 | 7/1999 |
| WO | WO 99/36510 | 7/1999 |

OTHER PUBLICATIONS

Cibelli JB, Cloned transgenic calves produced from nonquiescent fetal fibroblasts, 1998, Science, vol. 280, pp. 1256-1258.*
Schnieke AE, Human factor IX transgenic sheep produced by transfer of nuclei from transfected fetal fibroblasts, 1997, Science, vol. 278, pp. 2130-2133.*
Westhusin ME, Cloning to reproduce desired genotypes, 2000, Theriogenology, vol. 55, pp. 35-49.*
Concalves M, A concise peer into the background, initial thoughts, and practices of human gene therapy, 2005, BioEssays, vol. 27, pp. 506-517.*
Parekh-Olmedo H, Gene therapy progress and prospects: targeted gene repair, 2005, Gene Therapy, vol. 12, pp. 639-646.*
Verma IM, Gene Therapy: Twenty-first century medicine, 2005, Annu. Rev. Biochem. vol. 74, pp. 711-738.*
James Y, A novel gene delivery system using urothelial tissue engineered neo-organs, 1997, J. of Urology, vol. 158, pp. 1066-1070.*
Vogel et al. 2003, Science, vol. 300, pp. 225 and 227.*
Simerly et al. 2003, Science, vol. 300, p. 297.*
Mitalipov et al. 2006, Methods in Mol. Bio, vol. 348 pp. 151-168.*
Keefer CL, 2008, Theriogenology, vol. 69, pp. 48-54.*
Schieke et al., 1997, Science, vol. 278, pp. 2130-2133.*
Thompson et al., Reprod. Supp., 2003, vol. 61, pp. 495-508.*
Denning, Cloning and Stem Cells, 3:221-231, 2001.*
Westhusin et al., 2001, Theriogenology, vol. 55, pp. 35-49.*
Humble RJ, Can J Comp Med Vet Sci. Nov. 1954; 18(11): 379-389.*
Benichou et al., 2007, Frontiers in Bioscience, vol. 12, pp. 4362-4369.*
2004, Hipp et al., J. Exp. Clin. Asst. Reprod., vol. 1(3), pp. 1-10.*
2006, Tecirlioglu et al., Stem Cell Rev., vol. 2, pp. 277-287.*
Katzenstein et al. article entitled "Haploidentical related umbilical cord blood stem cell transplant in a child with acute non-lymphocytic leukemia" *Bone Marrow Transplantation* (1997) vol. 19, pp. 765-769.
Colman et al. article entitled "Therapeutic cloning: concepts and practicalities" *Tibtech* May 2000 (vol. 18) pp. 192-196.
Cibelli et al. article entitled "Cloned Transgenic Calves Produced from Nonquiescent Fetal Fibroblasts" *Science* vol. 280, pp. 1256-1258, 1998.
Schnieke et al. article entitled "Human Factor IX Transgenic Sheep Produced by Transfer of Nuclei from Transfected Fetal Fibroblasts" *Science* vol. 278, pp. 2130-2133, 1997.

* cited by examiner

*Primary Examiner* — Peter Paras, Jr.
*Assistant Examiner* — David Montanari
(74) *Attorney, Agent, or Firm* — K&L Gates LLP

(57) ABSTRACT

The present invention relates to a method for recombinant manufacturing of substances, wherein cells are transformed suing a nucleotide sequence coding for the substance, the transformed cells are subjected to a cloning process, and the cells obtained in this fashion are introduced into a host organism. The present invention relates in particular to the use of the method in the production of recombinant proteins, cells and tissues. According to a further aspect, the invention relates to a method, wherein the cells of an individual are isolated, said sells are introduced into an immunoincompetent animal for further growth and the cells, tissue and/or organs cultivated in the animal are again isolated and introduced into an individual.

4 Claims, No Drawings

SEQUENCE LISTING

```
<160> NUMBER OF SEQ ID NOS: 5

<210> SEQ ID NO 1
<211> LENGTH: 21
<212> TYPE: DNA
<213> ORGANISM: Artificial Sequence
<220> FEATURE:
<223> OTHER INFORMATION: Synthesized: primer 377L2/f

<400> SEQUENCE: 1
caggtgtcct ctctgacatc g                                              21

<210> SEQ ID NO 2
<211> LENGTH: 17
<212> TYPE: DNA
<213> ORGANISM: Artificial Sequence
<220> FEATURE:
<223> OTHER INFORMATION: Synthesized: primer 377R2

<400> SEQUENCE: 2
cgcagagtcc acagagg                                                   17

<210> SEQ ID NO 3
<211> LENGTH: 22
<212> TYPE: DNA
<213> ORGANISM: Artificial Sequence
<220> FEATURE:
<223> OTHER INFORMATION: Synthesized: primer 246

<400> SEQUENCE: 3
gaagacccca ttttgtccca ag                                             22

<210> SEQ ID NO 4
<211> LENGTH: 20
<212> TYPE: DNA
<213> ORGANISM: Artificial Sequence
<220> FEATURE:
<223> OTHER INFORMATION: Synthesized: primer 251

<400> SEQUENCE: 4
gtcccgaggt agatcttccc                                                20

<210> SEQ ID NO 5
<211> LENGTH: 20
<212> TYPE: DNA
<213> ORGANISM: Artificial Sequence
<220> FEATURE:
<223> OTHER INFORMATION: Synthesized: primer 248
```

```
<400> SEQUENCE: 5
gatgcttctc tattcctctg                                        20
```

SOMATIC CLONING GENE TRANSFER FOR THE PRODUCTION OF RECOMBINANT PROTEINS, CELLS AND ORGANS

The instant application is a 371 of PCT/EP00/07239, filed on Jul. 27, 2000.

The present invention relates to a process for recombinant manufacturing of substances in which cells are transformed using a nucleotide sequence coding for the substance, the transformed cells are subjected to a cloning process, and the cells so obtained are incorporated into a host organism. The present invention relates in particular to the use of the method in the production of recombinant proteins, cells and tissues. According to a further aspect, the invention relates to a method, wherein cells of an individual are isolated, these cells are introduced into an immunoincompetent animal for further growth, and the cells, tissue and/or organs cultivated in the animal are again isolated and introduced into an individual.

With the ascendance of recombinant gene technology biological systems were increasingly involved for manufacturing useful substances. With definition of the nucleotide sequence of the human genome it can be expected that discovery of new proteins and their role in the human body will be promoted and accelerated so that in the near future a number new substances for medical or other purposes will be available, whose manufacture is desirable. Nevertheless, use of existing in vitro cell culture systems for this purpose includes the drawback that until optimal production of the particular substances at least 1 to 2 years lapse. Moreover, handling such systems is complicated, subject to disturbances and cost-intensive. Thus, for instance, one of the major difficulties in large-scale operation of cell culture systems is the risk of contamination of the culture solution.

In recent years animals have been increasingly used for producing substances of industrial and pharmaceutical interest. To do this, along with the creation of so-called germ-line transgenic animals somatic gene transfer is used, wherein DNA coding for a particular substance is introduced into the somatic cells of a target individual. This can be done either in vivo; that is, in the entire organism or in vitro or in the laboratory into cells that have been harvested from the organism and after insertion of the construct into said cells, they are reintroduced into the organism. Expression of the construct is then induced in the animal so that the substance of interest can develop its effect in the animal.

The fact that the incorporated gene is expressed or has an effect only in the individual treated and is limited to the lifetime of the transformed cells is an inherent drawback in the transfer of gene constructs in somatic cells. There is no transfer to subsequent generations.

In the case of somatic gene transfer, other frequently encountered problems, which can negatively affect the characteristics and/or the behavior of the target cells, include particularly the fact that sufficiently large number of specific target cells with stabile transfection are obtained frequently only after great effort and the randomness of the integration of the inserted construct. Furthermore, problems often occur with respect to inadequate expression of the polypeptide coded by the inserted construct, which along with the difficulties at the level of the DNA can also be associated with intra- and extra-cellular obstacles and must each be investigated. The problems described above, therefore, restrict the use of the applications of somatic gene transfer in biotechnology in the broadest sense and are especially significant in the production of livestock.

An object of the present invention therefore is the elimination of the drawbacks of the prior art and to provide a novel method for manufacturing particular substances of interest.

Said object is achieved by a method for recombinant manufacturing of substances in which in a first step cells are transformed using a nucleotide sequence coding for said substance, the transformed cells are subjected to a cloning process, and the cells obtained in the cloning step are introduced into a host organism.

The cells used in the first step of the method can be any cells isolated from the individual and which can be subjected to a cloning process. Examples of these are particularly fetal or adult fibroblasts, primitive germ cells, granulosa cells, thymocytes, spleen cells, liver cells, macrophages, testicular or ovarian cells, etc. The cells can be used as such, isolated, or in culture, whereby they can also be subjected to a cloning process prior to transformation.

According to a preferred embodiment, the cells used for the transformation are isolated from an already available cellular clone, a cell culture or from an organism. In the sense of the invention, a cell clone is defined as cultivated cells cloned in vitro, fetuses obtained by cloning, or cloned animals.

The cells are then transformed using a nucleotide sequence coding for the substance of interest. In this context, substances are defined as all substances synthesized in the body such a proteins, polysaccharides, lipids, etc. as well as cells, tissues and organs that exhibit the inserted nucleotide sequence. The nucleotide sequence coding for the substance is, therefore, not only a sequence directly coding the sequence but also a sequence that codes for different polypeptides/enzymes, which form the substance of interest within or outside of the cells. In the context of the present invention recombinant is defined as those genes, which for the animal were altered either exogenously or endogenously but were altered in their expression patterns by means of recombinant gene technology such as, for example, in their differentiation-specific expression pattern or quantity expressed.

All currently known techniques can be used for transformation such as physical, chemical or viral techniques. In view of a targeted integration of the construct at particular sites in the genome the use of homologous recombination is preferred. If large gene clusters are inserted into the host cell, then the use of artificial chromosomes is also possible. Cell hybrids, too, as are used in mapping, can be created and selected so that they include also specific chromosomal fragments from the target genome in addition to the production animal genome. This is particularly advantageous, when an entire system of the target genome is to be transferred such as, for example, the immunoglobulin gene system.

The cells are then subjected to a cloning process. Cloning processes are known and described, for example, in PCT/EP98/00230 (WO 99/36510) and PCT/EP98/00229 (WO 99/035906), which are included herein by reference. The cloned cells are then allowed to proliferate to a particular developmental stage in vivo and/or in vitro, to the fetus for example, and then incorporated into the host organism (Step c) of Claim 1). Likewise, the cloned cells are allowed to proliferate to the point that there is a certain differentiation, whereby already certain, differentiated cells are incorporated into the host organism.

The cloned cells are then inserted into a host organism, which can be an animal, an animal fetus, an animal embryo or an animal cell aggregate as well as cloned animals, cloned animal fetuses, cloned animal embryos and cell aggregates. According to a preferred embodiment, the original donor cells which are transformed and then subjected to a cloning process, are of the same genotype as the host organism.

An advantage of such a procedure is that an already available—that is, a stock host organism can be provided with cells in a very short time, preferably of the same genotype containing genes for novel expression and can produce recombinant substances. The time savings so realized in comparison to conventional germ line gene transfer up to obtaining animals ready for production can be up to 5 years. Furthermore, the present method, notwithstanding the time savings and the more rapidly produced production system and the consequent costs savings, is also more efficient, since the producing organisms can be generated more cost-effectively. Thus it is possible to use cells of a clone available in vitro, in addition to which already vital animals are available, as the original donor cells for the transformation and to introduce them after transformation and cloning into the host organism, which, because it is a clone, inherently has the same genotype.

A further advantage of the herein described somatic cloning gene transfer method is also the possibility of a quick response to new requirements or necessities in the case of expression of recombinant proteins. Normally, even when using a production animal species having a short generation interval, such as the rabbit, for example, 7 months can lapse after creation of the construct until sufficient material is available for the first studies of the expressing gene. A further year is required to production of the target polypeptide. In the case of cattle the process can take at least 3 to 4 years before the polypeptide of interests can be obtained by means of transgenic animals. In contrast, the method according to the invention makes it possible to considerably shorten the time for transforming cells using a novel construct in an already available host organism and obtaining the expression clone (the times is merely a couple of months).

The method according to the invention therefore makes it possible to obtain, in a timeframe comparable to that of in vitro cell culture, the first protein quantities for analysis, whereby according to the invention a production system is already additionally available that can be used for producing the target substance. The host organisms or animals can therefore be used quickly for manufacturing of the target substances.

In certain cases it is advantageous to prepare the host organism, which preferably is or is to be produced for stock, specifically for subsequent somatic cell gene transfer. This is particularly necessary if the applied transgenic or otherwise processed cells are to be provided with an advantage relative to the cells or structures present in the host organism, in order to obtain improved expression or manifestation.

For this purpose, certain cells, tissues or organs can be removed, for example, in the host organism, which can be done using a physical, chemical, immunological, molecular genetic or surgical procedure. Furthermore, animals or fetuses that are bred negative at specific gene loci are homozygote negative (screen out concept) or kept in stock and used as required.

One possibility for depleting certain cells, tissues, or organs in the host organism is to use already transgenic organisms containing the construct, which is under the control of a developmental stage-specific or inducible promoter. In the first instance, on activation of the promoter during the particular developmental stage a tissue specific protein is automatically generated which results in apoptosis or extinction of the particular cells; for example, diphtheria toxin. In the second instance, a suicide gene construct is activated, which has pre-programmed a suitable tissue-specific promoter by the application of a specific effector, such as tetracycline or ecdyson, which results in specific depletion of the cells, tissues or organs.

A simple possibility for preparing and propagating such organisms is their cloning, using which the construct, once introduced into the organism, can be securely passed on to progeny. It is clear that by doing this any cells, tissue or organs in the organism can be influenced as needed in their proliferation or development.

The removal of cells/tissues can be used as an example of depletion of certain cells, from which the milk gland normally develops. At the birth of an animal relatively few of these cells are present. They develop only in the course of the first gravidity and shortly before birthing there is a burst in proliferation and formation of the functional milk gland. Therefore, if these animal mammary gland stem cells, which are present only in low numbers, are removed in the early developmental stage of the host organism and the removed cells replaced by recombinant (transformed) cells of this type, which carry expression programming for synthesis of a particular recombinant substance, the result will be attained that in the animal organism obtained in this fashion the forming milk glands will develop from the applied transformed cells. Consequently, in the production animal the recombinant substance will also be expressed in the introduced mammary system. The time savings in such a procedure is about 3 years.

A further example is the total or partial removal of blood stem cells or the stem cells of the immune system from the host organism by irradiation, for example, or another process and their replacement by transformed stem cells that have been transformed according to the invention and subjected to a cloning process and make possible, for example, the expression of humanized antibodies (ABs) or AB fragments (bispecific AB, for example) or other animal or human blood factors. If, in the cloned stem cells the immunoglobulin genes of the animal have been replaced in vitro by those of the human being and if these cells are introduced into the host organism using the method according to the invention, then said host organisms form human-identical polyclonal antibodies that can be of great value in the treatment of human disease.

Furthermore, with the help of the method according to the invention an efficient and unproblematic production system can be provided for factors present in the animals but whose concentrations in said animals are too low for their collection to be economic interest. One example of this is the expression of several genes for heparin synthesis under very powerful promoters. Since heparin occurs naturally in the organism, no immunological reaction would be produced against the cells, which would preferably be of the identical genotype, nor against the product.

Recloning of the cells can be repeated at least three times. It has been found that cells can complete up to 150 divisions; in other words, the cells from the cloning process survive substantially longer than normal cells and can therefore also survive in the animal even after several cloning processes and express genes at least as long as the animal lives.

In similar fashion and further development of the above areas of application, cells can be harvested from an available animal and embryos, fetuses and in vitro cultured cell lines established. These cell lines are then genetically altered using known methods. The cells are then differentiated directly in the in vitro culture or after re-cloning isolated from fetal organs and introduced as "transgenes" or otherwise genotypical, homogenetic cells into the adult original donor organism. Since these cells, with the exception of the transgene, do not differ from the original animal, the cells are capable of establishing themselves in the animal and will produce, for example, recombinant substances according to the genetic transformation.

According to a further aspect, the invention also relates to a method for manufacturing cells, tissues or organs in animal organisms, in which in a first step cells from an individual are isolated, the cells are introduced into an immunoincompetent animal organism, the animal organism is bred, the cells growing in the organism are isolated and the isolated cells are introduced into an individual.

This method is particularly suited for culturing cells, tissues and organs, preferably of human origin, in animal organisms, because the cells in the animal host organism are increased or grow even to form tissues and organs.

According to a preferred embodiment, the cells of the original donor individual or the tissue or organs cultured therefrom are reinstated into the same individual from which they were harvested, whereby tissue or organs can be made available that are not rejected when reintroduced (transplantation) into the individual.

An immunoincompetent animal organism is defined as any animal or fetus or animal embryo/cell aggregate, that does not reject the cells derived from the original donor individual. Suitable for this purpose are organisms that have been rendered immunodeficient as well as organisms, which are in such an early stage of development, during which the developing immune system has not yet 'learnt' to differentiate between self and non-self. Therefore, if cells from the original donor individual are introduced into such a host organism, these cells will not be rejected but will be essentially recognized as self and appropriately further develop.

Therefore, preferably animal organisms that were maintained by cloning are suitable as animal host organisms. Thus it is possible to keep a plurality of fetuses or embryos or cell aggregates in stock and to process them as needed using the cells of the original donor individual. The fetuses/embryos/cell aggregates are then allowed to grow to a stage, in which they have produced the desired effect; up to developing a mature organ or tissue or even to the point of developing a sufficient quantity of cells of the original donor individual, for example. This tissue/organ or these cells are then harvested, for example, by taking the organ from the animal and transplanted into the original donor individual. Naturally, this may involve sacrificing the animal depending on the removal of the particular organ.

The cells of the original donor individual can be introduced into a conventional host organism. In this case it must be expected that the animal will form chimeras from the cells/tissue/organ with its own cells/tissue/organ. In order to assure that the only its 'self' cells are reintroduced into the original donor individual, the particular overall tissue/organ/cells can be isolated and the animal cells separated, which can be accomplished, for example, by marking using antibodies against the animal cells and separation using FACS (fluorescence activated cell sorting).

According to a preferred embodiment, however, the affected cells/tissue/organs from the host organism are removed, which can be done as hereinbefore described.

Thus, for example, in a fetal host organism, in which the organ system is removed, the corresponding organ-specific stem cells of the original donor individual such as, for example, adult human stem cells that are harvested directly from the concerned organ, are introduced into the fetus and then replace the depleted cells and form the particular organ. When this is done, a chimerical organism is created, which receives a xenoorgan appropriate for transplantation. The affected organ represents a xenoorgan in the animal organism, which is not rejected in virtue of the absent immunocompetence of the fetus. After successful transplantation to the original donor individual—a human patient, for example—if human stem cells were used it would not be a xenogenic but an allogenic transplant or, if appropriate, even an autologous transplant, if the organ were created from adult stem cells of that particular individual/patient, which is possible in the case of certain organs and diseases notwithstanding the time requirement of approximately one year (kidney or liver, for example).

The use of the present method thus enables generating cells, tissues or organs within a short span of time so that even certain patients can be quickly provided with organs with a substantial or even absolute MHC type match. The method according to the invention, therefore, solves the currently existing problem of scarcity of available organs/tissues for transplantation.

The following examples explain the invention without limiting it. In the examples the harvesting of bispecific antibodies from the serum of non-transgenic cloned claves is described. The following steps were performed for creating calves with transgenic marrow cells, whereby reference is made to PCT/EP98/00230 (WO 99/36510) and PCT/EP98/00229 (WO 99/035906), which are included herein by reference.

1. Harvesting and genetic transformation of primary bovine fetal fibroblasts.
2. Cloning by nucleus transfer of transgenic embryos to host animals.
3. Harvesting the fetuses and isolation of transgenic bone marrow stem cells from the fetal liver.
4. Transfusion of these transgenic cells into available clone calves of the same chromosomal genotype.
5. Harvesting of serum by blood drawing.
6. Lysis of tumor cells by means of bispecific antibodies.

EXAMPLE 1

1. Harvesting/Genetic Transformation of Primary Bovine Fetal Fibroblasts (BOFFs)
a) Investigation of the Sensitivity of Bovine Fetal Fibroblasts (BOFFs) Versus Various antibiotics (selection marker).

BOFFs were semi-confluently plated and sensitivity tested in confrontation with neomycin (G418), hygromycin an puromycin relative to concentration and effect/time. Various preparations of BOFFs showed clear differences with respect to the required antibiotic concentrations (up to 2100×) in order to reach the $LD_{100}$. The time/effect window between and within preparations were in part strongly shifted. The best results were obtained using puromycin in a concentration of 1.5 µg/ml (3 5-fold concentration versus selection of stabile human or murine fibroblast cell lines).

Various transfection methods, which are conventionally used for transfecting established cell lines, were tested for their efficacy (antibiotic-resistant clones/transfection ratio) in BOFFs. The following were tested:

DOSPER (Roche, lipofection, polycationic lipids);
Lipofection Reagent (GIBCOBRL Life Technologies, Lipofection, polycationic lipids);
Lipofection Reagent (Clontech, lipofection, cationic and amphilic [sic] lipids);
Lipofection Reagent (Promega, lipofection, cationic and amphophilic lipids); $Ca_3(PO_4)_2$ DNA precipitates in the presence of 12% DMSO.

In contrast with establish fibroblast lines, which can be selected without difficulty in heavy dilution so that antibiotic resistant clones are generated, BOFFs cannot be plated below a certain critical density. In the selection for single-cell clones or in the case of growth from extreme dilution, in order to isolate individual clones, BOFFs either die out or go through one or more crises resulting in changes in morphology and/or proliferation behavior. The plating density was therefore chosen to allow optimal growth. However, this results in the antibiotic resistant cells representing a population and are not of clonal origin. By subsequent isolation and sub-cloning transgenic clonal cell lines are generated.

b) Transfection with ScFv and pJW6puro in BOFFs
Plasmids Used:

MAR::ScFv: The MAR sequences (chicken lysozyme gene matrix attachment regions; Castilla et al., Nat. Biotechnol. 16 (1998), 349) was cloned using ScFv in BlueScript (Stratagene). p77 (Brem et al., Theriogenology 43 (1995), 175) in pUC18 (Norander et al., Gene 26 (1983), 101).

pJW6puro (Morgenstern & Land, Nucleic Acids Res. 18, 1068) p77 and MAR::ScFv were linearized in order to assure a functional integration of the constructs. Based on the availability of restriction enzyme cleavage points the vector sequences could not be separated from the gene construct sequences. pJW6puro was transfixed circularly/supercoiled. The DNA quantities used or the ScFv: selection marker mixing ratio was 8:1 (2.5 µg p77+2.5 µg MAR::ScFv+0.6 µg pJW6puro=5.6 µg total DNA) or 3:1 (0.7 µg p77+0.9 µg MAR::ScFv+0.6 µg pJW6puro=2.2 µg total DNA).

When this was done, BOFF #32330201 p1 cells were used from which more than 1 year before transfection embryos and after transfer, clone calves (10 calves born) were generated. After treatment with trypsin the cell suspension was transferred into 10 mm culture plates and cultured using Dulbecco's modified Eagle's medium (Gibco, Grand Island, N.Y.), supplemented with 10% fetal calve serum (Biochrom, Berlin), 2 mM L-glutamine, 104 mM 2-mercapto ethanol, 2 mM non-essential amino acids (Sigma, St. Louis, Mo.), 100 IU/ml penicillin and 100 µg/ml streptomycin. The cells are cultured at 37° C. under 5% $CO_2$ in air until the cell sheet was sub-confluent (2 to 3 days) whereupon a part of this "0 passage" was frozen (10% dimethyl sufoxide, Sigma) and stored in liquid nitrogen.

Transfection preparations: BOFFs were plated prior to transfection sub-semiconfluently (approximately $5 \times 10^4$ $10^5$ cells) in 6-well culture dishes (Ø35 mm) (MEM, 15% FCS, 1×glutamine/penicillin/streptomycin). Transfection was done after setting and manifestation of fibroblast morphology by the cells. A transfection experiment was done for each Ø35 mm plate. TRANSFAST™ Lipofection:DNA:liposome ratio=1:2, incubation time 1.5 hour.

$Ca_3(PO_4)_2$ DNA precipitate transfection:
After an incubation time of 4 hours, transfection efficiency was augmented by the addition of 12% DMSO for 2 min (Müller et al., EMBO J. 12 (1993), 4221).

Selection, Establishment and Analysis of Transfectant Pools:

The selection medium was added 24 hours after transfection. After 2 days of section in 6-well culture plates the cells of one Ø35 mm well were divided 1:150 on a 24-well plate (concentration $28 \times 10^2$ cells/plate) Selection was continued until there was sub-confluent growth with Puro®BOFFs on the plate (49 days). The pools were expanded, cryopreserved and tested for successful transfection with p77 MAR::ScFv using PCR.

Screening for ScFv Transfectants:
Primer: 377L2/f 5'CAGGTGTCCTCTCTGACATCG3' (SEQ ID NO: 1) and
377R2 5'CGCAGAGTCCACAGAGG3' (SEQ ID NO: 2) (Annealing temperature, 66° C.; 1 kb amplificate)
Screening for p77 Transfectants:
Primer: 246 5'GAAGACCCCATTTTGTCCCAAG3' (SEQ ID NO: 3) and 251 5'GTCCCGAGGTAGATCTTCCC3' (SEQ ID NO: 4) (Annealing Temperature, 62° C.; 2.5 kb Amplificate)
Primer: 248 5'GATGCTTCTCTATTCCTCTG3' (SEQ ID NO: 5) and
251 5'GTCCCGAGGTAGATCTTCCC3' (SEQ ID NO: 4) (Annealing temperature, 60° C.; 1.2 kb amplificate)

PCR Results:
Lipofection Reagent lipofection: with both tested DNA ratios no p77/MAR::ScFv positive pools.
$Ca_3(PO_4)_2$ DNA precipitate transfection: DNA of interest: selection marker=3:1: no p77/MAR::ScFv positive pools.
$Ca_3(PO_4)_2$ DNA precipitate transfection: DNA of interest: selection marker=8:1 (Pool 3): 6 of 24 pools positive for p77 and MAR::ScFv characterization of the positive clone/pool: A3, B2, B3, C2, C3, C6 (strong signal).

EXAMPLE 2

The animals were cloned according to the method descried in PCT/EP98/00229 and the transgenic embryos were transferred to the host animals.

EXAMPLE 3

Harvesting of the fetuses and isolation of transgenic bone marrow stem cells from the fetal liver.

Transgenic bovine fetuses were harvested in the second trimester of gravidity. In this period, the hepatolineal period of fetal development, the liver is the principal site of blood formation and the locus of stem cells of all blood cells, the hemocystoblasts. The B lymphocytes develop from these hemocystoblasts after migration into the marrow cavity of the bones in the course of lymphocytopoiesis. The fetal liver is harvested aseptically and placed in RPMI medium with 4 gentamycin sulfate and 200 IU/ml heparin as an anticoagulant. Separation of the individual cells is done under strictly sterile conditions.

EXAMPLE 4

Transfusion of the transgenic cells into clone calves of the same chromosomal genotype.

Transplantation of the fetal hematopoietic cells is done in a suspension of physiological saline solution or medium by intravenous catheter infusion (14 gauge, 1.7 mm×64 mm, Teruno Co., Ltd).

EXAMPLE 5

Harvesting and purification of serum by blood drawing.
Blood is collected in regular intervals after transfusion of the transgenic blood cells by puncture of the *Vena jugularis*. Serum is separated from the blood cells by centrifuging the blood (1000 xg, 30 min). Sodium azide (final concentration: 0.02%) is added to the serum and it is then filtered through a cellulose acetate filter (0.22 µm). The residue is adjusted to pH 7.2 using 1 M NaOH. For biscFV molecule cleanup, the culture residue is passed through a protein L-agarose column (#20520 Pierce, Rockford II, USA) that has been equilibrated using 0.1 M sodium phosphate buffer (protein L binds human IgG, in particular single chain variable elements (ScFv) but not bovine IgG1 and IgG2). After application of the culture residue, the column bed is washed with 0.1 M phosphate buffer. The bound proteins are eluted using a 0.1 M glycine buffer stepwise at pH 3.0 and 2.0. The collected eluate is dialyzed over night against PBS, 0.22 µm sterile filtered and stored at 4° C.

EXAMPLE 6

Lysis of tumor cells using bispecific antibodies.

The biological activity of the bispecific antibodies is tested in the cytotoxicity test using 5,000 SKMe163 or M21 tumor cells. These two melanoma cell lines are strongly positive for the HMWG (high molecular weight glycoprotein) target antigen, which is recognized by the 9.2.27 monoclonal antibody (only the scFv portion). Peripheral blood lymphocytes (PBLs harvested fresh from healthy human donors and isolated by Ficoll gradient). are added to the target cells in a ratio of 10:1. Then 150 µg/ml chemically conjugated bsF(ab')2 with 9.2:27×CD3 specificity (melanoma×T lymphocyte in all cell culture plates for panclonal stimulation of all T lymphocytes, at this concentration alone it exhibits no mitogenic properties) is added. then the recombinant biscFv molecules purified from the serum are added directly. The total volume of the experimental preparation per cell culture plate in the microtitre plate is 150 µl. The plate is incubated for 5 days in the incubator at 37dc/5% $CO_2$. The non-adhering blood lymphocytes are removed after multiple washings with PBS so that only the residual adherent tumor cells remain in the cell culture dishes (visual inspection). 100 µl of fresh medium and 10 µl of the cell proliferation stain WST (Boehringer Mannheim, <Category>Abbreviation. No 1644 807) is added to the cell culture dishes. Incubation then follows (47dc/5% $CO_2$) in the incubator for 1 to 4 hours and which is then followed by evaluation by ELISA reader (480 nm). Visual assessment and the low optical density show 100% tumor cell killing. This demonstrates that recombinant bispecific antibodies produced in transgenic blood cells are highly efficient.

The invention claimed is:

1. A method for manufacturing a recombinant protein, comprising the steps of
   a) isolating fibroblast cells;
   b) transfecting the isolated fibroblast cells with a plasmid comprising a nucleotide sequence coding for the recombinant protein;
   c) isolating a nucleus from the transfected fibroblast cells;
   d) injecting the isolated nucleus into an enucleated bovine oocyte that is genetically identical to the isolated fibroblast cells;
   e) stimulating the oocyte to divide and form an embryo;
   f) introducing the embryo into a host bovine;
   g) allowing the embryo to develop into a fetus in the host bovine;
   h) harvesting the fetus from the host bovine;
   i) isolating cells from the fetus;
   j) introducing the isolated cells in a bovine animal;
   k) expressing the recombinant protein in a bovine animal; and
   l) obtaining the expressed recombinant protein from the bovine animal.

2. The method according to claim 1, wherein the isolated fibroblast cells are subjected to a cloning process prior to the transfection.

3. The method according to claim 1, wherein the isolated fibroblast cells are isolated from an existing cell clone.

4. The method according to claim 1, wherein mammary gland stem cells or hematopoietic stem cells are depleted from the bovine animal and are replaced by recombinant cells of the same type.

* * * * *